United States Patent
Ye et al.

(10) Patent No.: US 9,420,974 B2
(45) Date of Patent: Aug. 23, 2016

(54) METHOD AND APPARATUS FOR ATTENUATION CORRECTION

(75) Inventors: Jinghan Ye, Fremont, CA (US); Hongjie Liang, San Jose, CA (US); John Vesel, Kirtland, OH (US); David Sowards-Emmerd, Sunnyvale, CA (US); Lingxiong Shao, Saratoga, CA (US); Jody L. Garrard, Elk Grove, CA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 361 days.

(21) Appl. No.: 12/995,679

(22) PCT Filed: May 29, 2009

(86) PCT No.: PCT/IB2009/052284
§ 371 (c)(1),
(2), (4) Date: Dec. 2, 2010

(87) PCT Pub. No.: WO2009/147607
PCT Pub. Date: Dec. 10, 2009

(65) Prior Publication Data
US 2011/0081067 A1    Apr. 7, 2011

Related U.S. Application Data

(60) Provisional application No. 61/059,366, filed on Jun. 6, 2008.

(51) Int. Cl.
*G06K 9/00* (2006.01)
*A61B 6/03* (2006.01)
(Continued)

(52) U.S. Cl.
CPC ............. *A61B 6/032* (2013.01); *A61B 6/037* (2013.01); *A61B 6/466* (2013.01); *A61B 6/5235* (2013.01); *G01T 1/1611* (2013.01); *A61B 6/503* (2013.01); *A61B 6/541* (2013.01)

(58) Field of Classification Search
USPC ............................................. 382/131
See application file for complete search history.

(56) References Cited

U.S. PATENT DOCUMENTS

| | | | | |
|---|---|---|---|---|
| 6,092,928 A | * | 7/2000 | Mattson | A61B 6/08 378/197 |
| 6,370,217 B1 | * | 4/2002 | Hu | A61B 6/541 378/8 |

(Continued)

FOREIGN PATENT DOCUMENTS

| | | |
|---|---|---|
| JP | H06269445 A | 9/1994 |
| JP | H09005441 A | 1/1997 |
| WO | 2008024584 A2 | 2/2008 |

OTHER PUBLICATIONS

Kinahan, Paul., X-ray Based Attenuation Correction for PET, 2003, Seminar in Nuc Med vol. XXXIII, No. 3 (Jul. 2003, pp. 166-179.*

(Continued)

*Primary Examiner* — Chan Park
*Assistant Examiner* — Iman K Kholdebarin

(57) ABSTRACT

A method and apparatus of image reconstruction attenuation correction in PET or SPECT cardiac imaging is provided. A volumetric attenuation imaging scan by an X-ray source may be used to generate a gamma ray attenuation map. The volumetric attenuation imaging scan may be randomized, and may be performed while the imaged subject is breathing.

24 Claims, 3 Drawing Sheets

(51) Int. Cl.
*A61B 6/00* (2006.01)
*G01T 1/161* (2006.01)

(56) References Cited

U.S. PATENT DOCUMENTS

| | | | | |
|---|---|---|---|---|
| 6,388,244 | B1* | 5/2002 | Gagnon | G01T 1/1615 250/208.1 |
| 6,429,433 | B1* | 8/2002 | Gagnon | G06T 1/1648 250/363.01 |
| 6,461,040 | B1* | 10/2002 | Mattson | A61B 6/08 378/205 |
| 6,841,782 | B1* | 1/2005 | Balan | A61B 6/032 250/363.02 |
| 2005/0058259 | A1* | 3/2005 | Vija | A61B 6/505 378/210 |
| 2007/0003014 | A1* | 1/2007 | Boese | A61B 6/12 378/95 |
| 2007/0081704 | A1 | 4/2007 | Pan et al. | |
| 2007/0110212 | A1* | 5/2007 | Li | A61B 6/025 378/25 |
| 2007/0297660 | A1* | 12/2007 | Hsieh | A61B 6/032 382/131 |
| 2008/0156993 | A1* | 7/2008 | Weinberg | A61B 6/12 250/363.03 |
| 2008/0237476 | A1* | 10/2008 | Uribe | G01T 1/1611 250/363.04 |
| 2009/0087065 | A1* | 4/2009 | DaSilva | A61B 6/037 382/131 |
| 2011/0081067 | A1* | 4/2011 | Ye | A61B 6/032 382/131 |
| 2014/0177934 | A1* | 6/2014 | Noshi | A61B 6/0407 382/131 |

OTHER PUBLICATIONS

Pan, T., et al.; Attenuation Correction of PET Images with Respiration-Averaged CT Images in PET/CT; 2005; pp. 1481-1487; http://jnm.snmjournals.org/cgi/reprint/46/9/1481.pdf.

Utsunomiya, D., et al.; Object-specific Attenuation Correction at SPECT/CT in Thorax: Optimization of Respiratory Protocol for Image Registration; 2005; Radiology; vol. 237:662-669.

Kinahan, P. E., et al.; X-ray-Based Attenuation Correction for Positron Emission Tomography/Computed Tomography Scanners; 2003; Seminars in Nuclear Medicine; 33(3)166-179.

* cited by examiner

METHOD AND APPARATUS FOR ATTENUATION CORRECTION

CROSS REFERENCE TO RELATED APPLICATIONS

This application claims the benefit of U.S. provisional application Ser. No. 61/059,366 filed Jun. 6, 2008, which is incorporated herein by reference.

The present application relates generally to the imaging arts and more particularly to the generation of attenuation maps for use in electronic image reconstruction. It has application at least in combined PET/CT or SPECT/CT imaging systems, most especially used for cardiac imaging, and will be described with particular reference thereto. However, it may also find more general application in generating attenuation maps for use with other types of imaging, and in other arts.

PET (Positron Emission Tomography) and SPECT (Single Photon Emission Computed Tomography) are typically used to generate diagnostic images of relatively dynamic processes in a person's body, such as metabolic activity or blood flow. In PET and SPECT, a radioactive isotope produces gamma rays which pass through the subject's body to be detected by a gamma ray detector. Often the radioactive isotope is administered as a radiopharmaceutical inside a subject's body. The gamma ray detector typically records projected gamma ray images at different angular positions around a central axis. To accomplish this, the gamma ray detector may either be rotated around the axis (as is common in SPECT), or may be a ring or partial ring extending around the axis (as is common in PET), or have some other configuration. The detector typically interacts with gamma rays to produce electronic signals representative of the gamma ray spectrum received by the detector. The electronic signals may then be processed to produce a PET or SPECT image of the subject's body.

Computed Tomography (CT) is typically used to generate diagnostic images of relatively static structure in a person's body, such as bone. In CT, an X-ray source disposed externally to the subject's body produces X-rays which pass entirely through the subject's body to be detected by a detector disposed approximately on the opposite side of the subject's body from the X-ray source. The X-ray source and X-ray detector are typically rotated together around the imaged subject to record projected X-ray images at different angular positions around a central axis. The detector typically interacts with X-rays to produce electronic signals representative of the X-ray spectrum received by the detector. The electronic signals may then be processed to produce a CT image of the subject's body.

Combined PET/CT or SPECT/CT imaging systems include hardware and software for generating PET or SPECT images, and for generating CT images. A PET or SPECT image may be overlaid with a CT image to form one combined image. This combination process is called "registration" of the PET or SPECT image with the CT image. Such registration occurs in clinical or medical treatment, pre-clinical research, scientific or technical analysis of objects and processes, and in other contexts.

One challenge faced in PET, SPECT and CT is correcting for attenuation of the gamma rays (in PET and SPECT) or X-rays (in CT) within the imaged subject. Gamma rays and X-rays interact with tissue or other material disposed between the radiation source and the radiation detector. That interaction typically prevents some gamma rays and some X-rays from reaching the detector (attenuation) and changes the direction of some gamma rays and some X-rays (scatter). The degree of attenuation and scatter will vary from patient to patient and depends upon the physical characteristics of the matter (i.e., bone, muscle, organ tissue, etc.) between the radiation source and the radiation detector. Such attenuation and scatter should be accounted for in generating highly accurate quantitative PET, SPECT or CT diagnostic images.

This may be accomplished by use of an attenuation map of the imaged subject. Such an attenuation map estimates the density of various regions in the imaged subject with respect to the radiation at issue, whether gamma rays (in PET and SPECT) or X-rays (in CT). Regions having a relatively high density are more likely to cause attenuation than regions having a lower density. The attenuation map may be used to correct the imaging data actually recorded by the detectors to account for data lost as a result of attenuation.

In that regard, it is known to generate a gamma ray attenuation map using X-ray attenuation data. From the known X-ray spectrum of the external X-ray source, and the X-rays actually recorded by the X-ray detector at various angular positions around a central axis of the imaged subject, an X-ray attenuation map of the subject may be generated. X-ray attenuation within an imaged subject during CT imaging is qualitatively similar to gamma ray attenuation within the imaged subject during PET or SPECT imaging. For example, both X-rays and gamma rays are attenuated more by bone than by softer tissue. As a result, the X-ray attenuation map generated by the CT imaging data can be used to estimate or approximate a gamma ray attenuation map for PET or SPECT imaging.

One difficulty in this process lies in registering the CT attenuation data with the PET or SPECT imaging data, especially if the respective data sets are taken in succession and not simultaneously, as is often the case. Any misalignment of the two data sets provides erroneous information in the gamma ray attenuation map which impairs the diagnostic value of the reconstructed PET or SPECT images. This difficulty is particularly acute when imaging the upper portion of a person's torso, for example in cardiac imaging. In such cases the person's respiratory motions can cause the imaged areas to move as much as about 3 cm or more while the imaging data is being recorded. Such movement complicates the registration process.

Some conventional cardiac imaging systems use the X-ray data from a diagnostic CT imaging scan to generate an attenuation map for use in correcting PET or SPECT images. However, to improve the diagnostic quality of CT images in cardiac imaging, the patient is typically asked not to breathe and to hold his or her breath during the imaging scan. These scans usually last up to about two or three seconds, and most people can comfortably hold their breath for that long. Doing so maintains the heart and lungs in a relatively constant position during the entire CT imaging scan, which simplifies the CT image reconstruction process after the imaging scan is completed. By contrast, cardiac PET and SPECT diagnostic imaging scans take a longer time, on the order of a few minutes (e.g. 3-6 minutes for cardiac PET, or 10-15 minutes for larger scans). Most people are not able to hold their breath for that amount of time. Thus, using an attenuation map generated from the CT diagnostic image data (during which the subject is holding his or her breath) for attenuation correction of a diagnostic PET or SPECT image (during which the subject is breathing) can lead to undesirable artifacts appearing in the diagnostic PET or SPECT image. This is especially true for cardiac imaging, or for chest imaging near the diaphragm.

In part to overcome such shortcomings, other conventional cardiac imaging systems perform a slow rotation X-ray scan to generate an attenuation map for use in correcting PET or SPECT images. These slow rotation X-ray scans usually about 4 minutes, adding significantly to the overall acquisition time, but the subject is not required to hold his or her breath during the scan. However, these conventional systems are not volumetric (discussed further below), so it is necessary to move the imaged subject during the X-ray imaging process in order to image the entire cardiac region. That movement of the subject, combined with the subject's own movements in breathing, complicates the registration process and can lead to undesirable artifacts appearing in the attenuation map.

According to one aspect of the present invention, a method and apparatus are provided for improved attenuation correction during imaging. The method and apparatus are especially useful in cardiac PET or SPECT imaging, but may be used in other contexts as well.

One advantage resides in a more accurate and robust attenuation correction, reducing the risk of visible artifacts appearing in PET and SPECT images. Another advantage resides in producing more useful PET and SPECT images. Numerous additional advantages and benefits will become apparent to those of ordinary skill in the art upon reading the following detailed description of preferred embodiments.

The invention may take form in various components and arrangements of components, and in various process operations and arrangements of process operations. The drawings are only for the purpose of illustrating preferred embodiments and are not to be construed as limiting the invention.

The imaging method and apparatus described here are directed generally to any imaging system which generates an attenuation map for one imaging modality (such as PET or SPECT) from data collected by another imaging modality (such as CT). One example of such an apparatus is the combined SPECT/CT imaging system 100 shown in FIGS. 1 and 2. As already mentioned, the imaging method and apparatus disclosed here have application in various other kinds of imaging systems.

Figure 1:
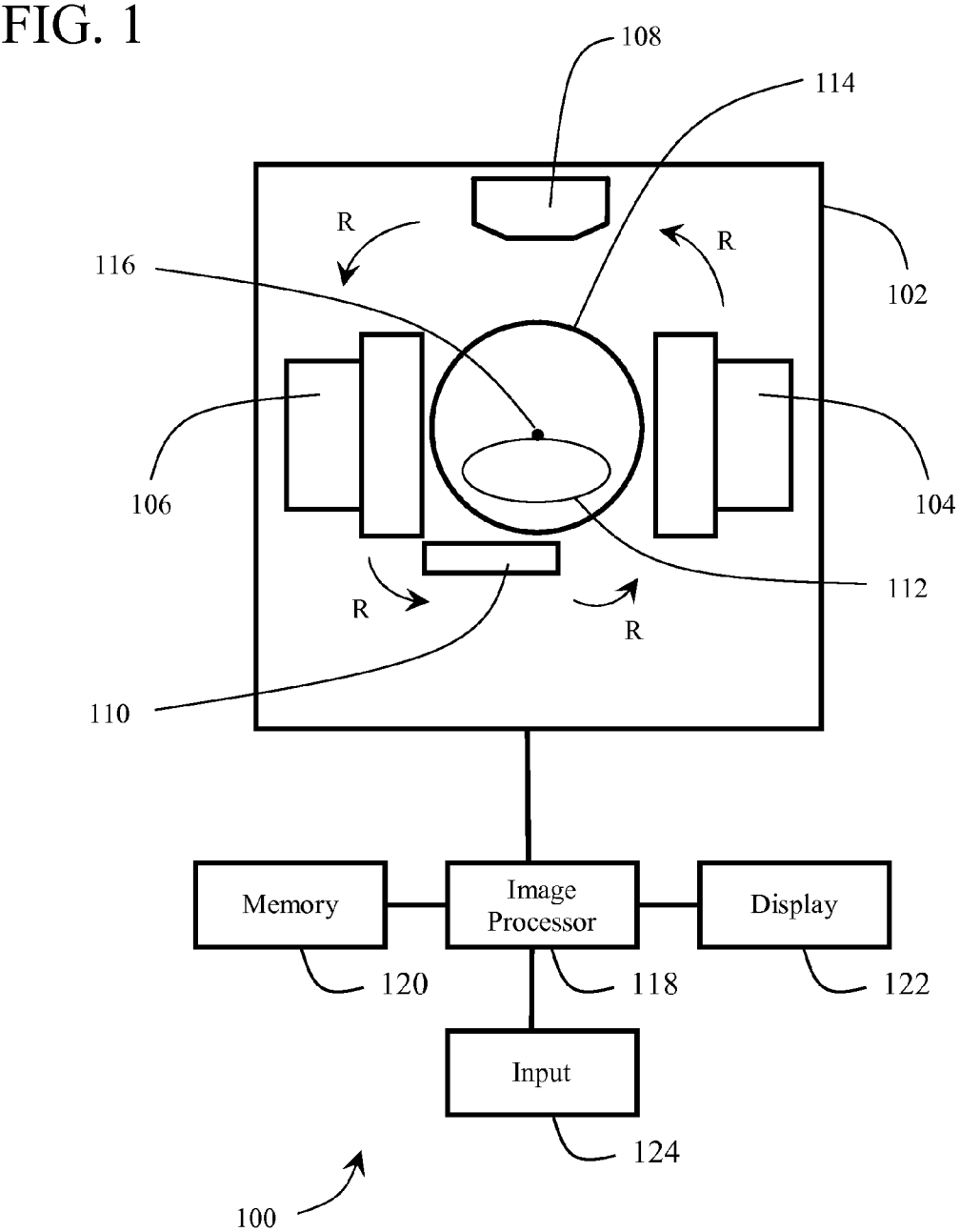
FIG. 1 is a schematic front view of a combined SPECT/CT imaging system.
Figure 2:
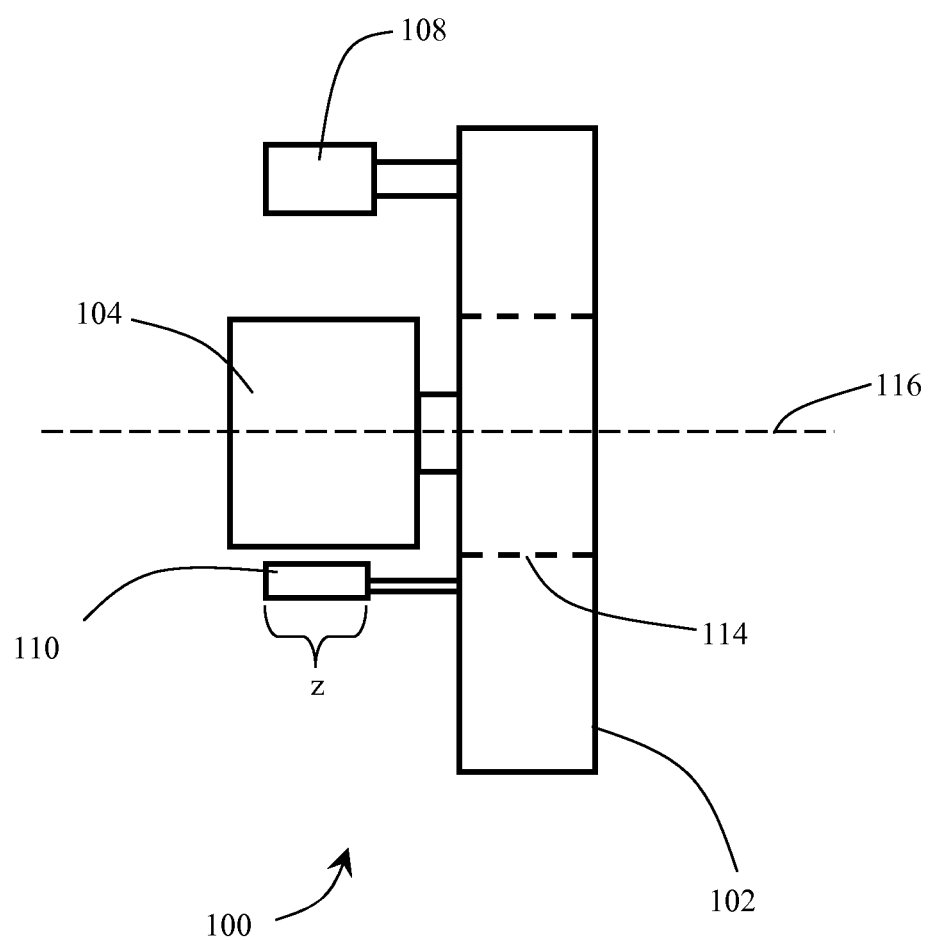
FIG. 2 is a side view of the imaging system of FIG. 1.

As illustrated in FIGS. 1 and 2, the system 100 includes a gantry 102 which holds two SPECT gamma ray detectors 104 and 106, an X-ray source 108 and a flat panel X-ray detector 110. A representative subject to be imaged is shown at 112 in FIG. 1, partially received in an aperture 114 in the gantry 102. The two gamma ray detectors 104 and 106, the X-ray source 108, and the X-ray detector 110 all rotate together at the same time on the gantry 102 around an axis of rotation 116. This is illustrated by the arrows R in FIG. 1. However, the detectors do not acquire data at the same time. When the X-ray detector 110 is gathering data for CT imaging, the gamma ray detectors 104 and 106 are not gathering data for SPECT imaging. When the gamma ray detectors 104 and 106 are gathering data for SPECT imaging, the X-ray detector 110 is not gathering data for CT imaging.

The imaged subject 112 usually lies down or is placed upon a table or other support (not shown) extending along the longitudinal axis 116. The table or other support is usually moveable along that axis 116 so that the imaged region(s) of the subject 112 may be disposed proximate to the detectors 104, 106 and 110. As the detectors 104, 106 and 110 rotate around the axis of rotation 116 during an imaging operation, they record several "projections." A projection is an image recorded by a detector at a specified angular position around the axis of rotation 116. For example, projections may be recorded in 1° intervals or 2° intervals as the detectors rotate around the axis 116.

In PET systems, by contrast, the gamma ray detector is typically formed as a complete or partial ring of detector arrays disposed around an axis. In such situations, the detector arrays do not rotate. However, the angular position of each detector with respect to the central axis is recorded in order to track projection data.

Such projection data is stored by an imaging data processor 118 in a memory 120. Once all the projection data is gathered, it may be electronically processed by the imaging data processor 118. The processor 118 generates an image of the subject 112, according to a mathematical algorithm or algorithms, which can be displayed on an associated display 122. For example, the processor 118 receives X-ray data from the X-ray detector 110 to generate CT images, and receives gamma ray data from gamma ray detectors 104 and 106 to generate SPECT images. The processor 118 also combines such data to generate SPECT/CT images. A user input 124 may be provided for a user to control the processor 118. Similar components can be used in PET/CT systems.

The aforementioned functions can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as memory 120, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the memory 120. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

In the SPECT/CT system 100 of FIGS. 1 and 2, a rotating frame (not shown) which holds the detectors 104, 106 and 110 on the gantry 102 may rotate at variable speeds. In this way the frame may rotate at a first relatively high speed to position the X-ray source 108 and the X-ray detector 110 for diagnostic CT imaging. And it may also rotate at a second relatively lower speed to position the gamma ray detectors 104 and 106 for diagnostic SPECT imaging. In an alternative embodiment, the X-ray source 108 and X-ray detector 110 may be disposed on a first rotating frame, with the gamma ray detectors 104 and 106 disposed on a second rotating frame which is separate from the first rotating frame.

The X-ray source 108 and X-ray detector 110 of the SPECT/CT system 100 are configured to perform "volumetric" imaging scans. In a volumetric system, the transaxial field of view "z" of the X-ray detector 110 along the axis of rotation 116 is sufficiently large that the imaged subject 112 need not be moved along that axis 116 in order to generate a complete image of the region(s) of interest in the imaged subject 112. For example, in cardiac imaging the region of interest is the heart of the imaged subject 112. Thus, in a volumetric cardiac imaging system, the length "z" of the X-ray detector 110 as shown in FIG. 2 is at least as long as the subject's heart. As another example, if the subject's entire respiratory region were to be imaged, then in a volumetric system the length "z" would be at least as long as the subject's lungs. The geometry of the SPECT/CT system 100 shown in FIGS. 1 and 2 is useful in this regard, as the flat panel X-ray detector 110 is offset from the axis of rotation 116, leading to a larger transaxial field of view "z".

Figure 3:
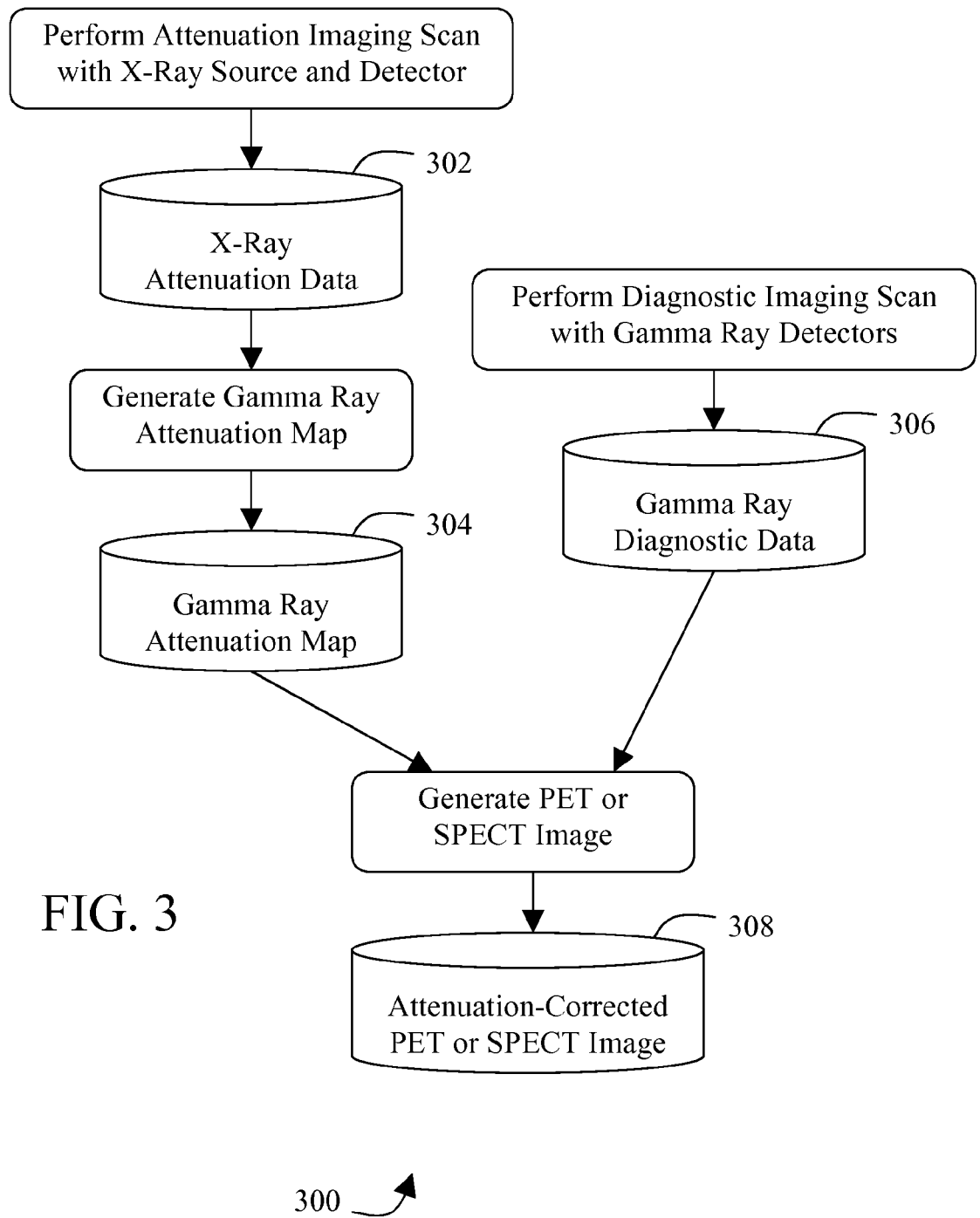
FIG. 3 illustrates a process of generating an attenuation map for use in PET or SPECT imaging from CT image data.

An attenuation map for use in SPECT imaging by the system 100 may be generated in a process 300 as follows, and shown in FIG. 3. The X-ray source 108 and X-ray detector 110 are used to perform an attenuation imaging scan and generate X-ray attenuation data 302. This attenuation X-ray imaging scan may be a separate scan from the diagnostic X-ray imaging scan used to generate a CT image or it may be the same scan. The X-ray attenuation data 302 may be the same data used to generate a diagnostic X-ray image, or a subset of that data, or it may be an entirely different set of data from the diagnostic data, or a combination of diagnostic and non-diagnostic data. The X-ray attenuation data 302 is used to generate a gamma ray attenuation map 304 for use in generating a diagnostic SPECT image (and perhaps other purposes).

The attenuation imaging scan may be characterized by the number of rotation routines used to generate the X-ray data. In particular, the attenuation imaging scan may be either a single pass scan or a multiple pass scan. A single pass scan is one in which the X-ray source 108 and X-ray detector 110 go through only one imaging rotation around the rotation axis 116 to generate an attenuation map. Thus, in a single pass scan, at most only one X-ray measurement is taken at each angular position around the axis 116. A multiple pass scan is one in which the X-ray source 108 and X-ray detector 110 go through multiple imaging rotations around the rotation axis 116 to generate an attenuation map. Thus, in a typical multiple pass scan, multiple X-ray measurements are taken at each angular position. If the system makes five passes, all starting at the same angular position, then five X-ray measurements are taken at each projection. If the five passes start at different angular positions and extend less than 360° (as is typical), then some projections may be taken less than five times.

The attenuation imaging scan may also be characterized by the length of time of the scan. In particular, the attenuation imaging scan may be either a quick scan or a slow scan. A quick scan is one which is short enough in time that the subject may hold his or her breath during the entire imaging scan. Thus a quick scan usually lasts anywhere from less than one breathing cycle to about five breathing cycles, or even longer, depending on the subject's tolerance for holding his or her breath. In this context, a breathing cycle is one complete inhalation and expiration by the subject. For most subjects, a quick scan may range from about one breathing cycle to about two breathing cycles. A slow scan, by contrast, takes a longer time than a quick scan. A slow scan is one which is too long to permit the patient to hold his or her breath.

Whether the attenuation imaging scan is single pass or is multiple pass, or is quick or is slow, the subject may or may not be asked to actually hold his or her breath. In certain circumstances, it may be advantageous for the subject to be breathing and not holding his or her breath during the attenuation imaging scan. That is because the subject is breathing during the SPECT diagnostic imaging scan. Without being bound by theory, it is believed that generating an attenuation map from X-ray data while the subject is breathing more accurately corresponds to the actual attenuation experienced by gamma rays during the SPECT scan. Specifically, it is believed that the movements of the imaged region resulting from the subject's breathing are in effect averaged over multiple breathing cycles during the attenuation imaging scan, just as they are averaged during a SPECT scan. To improve the data set to be averaged, it may be desirable to randomize the attenuation imaging scan so that multiple measurements are recorded at each angular position. It is believed this improves the data set in generating the average, by increasing the possibility that different respiration phases will be counted at each angular position. As one example of one benefit which might be achieved with such randomization, it is believed that such randomization can provide a good respiratory sampling with a scan of only about 1 to 2 minutes, compared with a 4 minute scan time of known techniques. This same theory, and the benefits of randomization, also apply to PET/CT systems.

A first representative randomization technique employs a multiple pass scan by the X-ray source 108 and X-ray detector 110, at variable speeds, while the subject is breathing. For example, the first pass might be at a high speed of rotation. Then the second pass might be a slightly slower speed of rotation. Then the next pass might be slightly slower still, and so on, until the final and slowest pass is made. Or, alternatively, the first pass might be at a slow speed of rotation, which increases on each succeeding pass until a final and fastest pass is made. As another alternative, the speed may be varied by increasing and decreasing speeds between succeeding passes in a multiple pass scan.

A second representative randomization technique employs a multiple pass scan by the X-ray source 108 and X-ray detector 110, with respiratory gating. As is well known in the imaging arts, respiratory gating is the practice of monitoring the imaged subject's breathing to determine the occurrence of a triggering event, such as when the subject begins to inhale, or begins to exhale, or the like. In the context of an attenuation imaging scan, such a triggering event may be used to initiate each of a series of imaging scans, with the passes starting at varying angular positions. This second randomization technique may be combined with the first randomization technique, whereby for example each pass in the imaging scan is started at a different angular position when the patient begins to inhale, and the passes are also taken at variable speeds.

In a third randomization technique, a multiple pass scan by the X-ray source 108 and X-ray detector 110 is performed with the length of each pass varying. The first pass might be for example 90°, then the second pass goes 180°, and so on. This third randomization technique may be combined with the first randomization technique, the second randomization technique, or both.

Again referring to FIG. 3, once the gamma ray attenuation map 304 is generated, it may be used to correct the imaging data actually recorded by the gamma ray detectors 104, 106 to account for data lost due to attenuation. Thus, a gamma ray diagnostic imaging scan is performed with the detectors 104, 106 to generate gamma ray diagnostic data 306. Using that data 306 and the gamma ray attenuation map 304, a SPECT image 308 may be generated which is corrected for attenuation. A PET/CT system may also use the process 300 to generate a gamma ray attenuation map for PET imaging.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. The invention may take form in various components and arrangements of components, and in various steps and arrangements of steps. The drawings are only for purposes of illustrating the preferred embodiments and are not to be construed as limiting the invention.

Having thus described the preferred embodiments, the invention is now claimed to be:

1. A method of correcting a PET or SPECT image of an imaged subject for attenuation, the method comprising:
    performing a volumetric attenuation imaging scan of the subject with an X-ray source and an X-ray detector to generate volumetric X-ray attenuation imaging data, such that the imaged subject is not moved along an axis of rotation of the X-ray detector during the imaging scan, wherein the volumetric attenuation imaging scan is performed while the subject is breathing;
    randomizing the volumetric attenuation imaging scan, wherein randomizing the volumetric attenuation imaging scan comprises averaging volumetric X-ray attenuation imaging data collected during different breathing phases;
    using the volumetric X-ray attenuation imaging data to generate a gamma ray attenuation map;
    performing a gamma ray imaging scan of the subject with a gamma ray detector to generate PET or SPECT imaging data; and
    using the gamma ray attenuation map to correct the PET or SPECT imaging data for attenuation, and to generate an attenuation-corrected PET or SPECT image.

2. The method of claim 1, wherein the volumetric attenuation imaging scan is a multiple pass scan.

3. The method of claim 1, wherein the randomizing comprises performing multiple passes at varying rotational speeds.

4. The method of claim 1, wherein the randomizing comprises performing multiple passes and using respiratory gating to trigger a beginning of each pass at varying angular positions around a central axis.

5. The method of claim 1, wherein a cardiac area of the subject is imaged.

6. The method of claim 1, wherein the volumetric attenuation imaging scan is a slow scan.

7. The method of claim 1, wherein the X-ray source and the X-ray detector are mounted on a rotating frame which may rotate at variable speeds.

8. The method of claim 1, wherein the randomizing comprises averaging volumetric X-ray attenuation imaging data collected during multiple measurements at each angular position.

9. The method of claim 1, wherein the randomizing comprises performing multiple passes, and wherein each pass comprises a different length.

10. An apparatus for correcting a PET or SPECT image of an imaged subject for attenuation, the apparatus comprising:
    an X-ray source and an X-ray detector to perform a volumetric attenuation imaging scan of the subject to generate volumetric X-ray attenuation imaging data, such that the imaged subject is not moved along an axis of rotation of the X-ray detector during the imaging scan, wherein the volumetric attenuation imaging scan is performed while the subject is breathing;
    wherein the volumetric attenuation imaging scan is randomized, and wherein the volumetric X-ray attenuation imaging data comprises averaged volumetric X-ray attenuation imaging data collected during different breathing phases;
    a computer readable medium comprising logic to generate a gamma ray attenuation map using the volumetric X-ray attenuation imaging data;
    a gamma ray detector to perform a gamma ray imaging scan of the subject to generate PET or SPECT imaging data; and
    the computer readable medium comprising logic to use the gamma ray attenuation map to correct the PET or SPECT imaging data for attenuation, and to generate an attenuation-corrected PET or SPECT image.

11. The apparatus of claim 10, wherein the volumetric attenuation imaging scan is a multiple pass scan.

12. The apparatus of claim 10, wherein the randomizing comprises performing multiple passes at varying rotational speeds.

13. The apparatus of claim 10, wherein the randomizing comprises performing multiple passes and using respiratory gating to trigger a beginning of each pass at varying angular positions around a central axis.

14. The apparatus of claim 10, wherein a cardiac area of the subject is imaged.

15. The apparatus of claim 10, wherein the volumetric attenuation imaging scan is a slow scan.

16. The apparatus of claim 10, wherein the X-ray source and the X-Ray detector are mounted on a rotating frame which may rotate at variable speeds.

17. The apparatus of claim 10, wherein the randomizing comprises averaging volumetric X-ray attenuation imaging data collected during multiple measurements at each angular position.

18. The apparatus of claim 10, wherein the randomizing comprises performing multiple passes, and wherein each pass comprises a different length.

19. A method of generating an attenuation map for using in an imaging process utilizing a gamma ray source, the method comprising performing a randomized volumetric attenuation imaging scan of a subject using X-rays to generate volumetric X-ray attenuation imaging data, such that the imaged subject is not moved along an axis of rotation of the X-ray detector during the imaging scan, wherein performing the randomized volumetric attenuation imaging scan comprises averaging volumetric X-ray attenuation imaging data collected during different breathing phases, and using the volumetric X-ray attenuation imaging data to generate a gamma ray attenuation map.

20. The method of claim 19, wherein the volumetric attenuation imaging scan is performed while the subject is breathing.

21. The method of claim 20, wherein the volumetric attenuation imaging scan is a multiple pass scan.

22. The method of claim 19, wherein the randomizing comprises performing multiple passes at varying rotational speeds.

23. The method of claim 19, wherein the randomizing comprises performing multiple passes and using respiratory gating to trigger a beginning of each pass at varying angular positions.

24. The method of claim 19, wherein the cardiac area of the subject is imaged.

* * * * *